United States Patent [19]
Colombo et al.

[11] Patent Number: 4,822,528
[45] Date of Patent: Apr. 18, 1989

[54] 4-SUBSTITUTED 6-ALKYLIDENANDROSTEINE-3,17-DIONE DERIVATIVES AND PROCESS FOR THEIR PREPARATION

[75] Inventors: Maristella Colombo, Cesano Boscone; Franco Buzzetti, Monza; Enrico di Salle; Paolo Lombardi, both of Milan, all of Italy

[73] Assignee: Farmitalia Carlo Erba S.R.L., Milan, Italy

[21] Appl. No.: 86,608

[22] Filed: Aug. 18, 1987

[30] Foreign Application Priority Data

Sep. 17, 1986 [GB] United Kingdom ................ 8622330

[51] Int. Cl.$^4$ ...................... C07J 1/00; C07C 117/00
[52] U.S. Cl. ............................. 260/397.3; 260/397.4; 260/349
[58] Field of Search .................. 260/397.3, 397.4, 349; 514/177, 178

[56] References Cited

U.S. PATENT DOCUMENTS

| | | | |
|---|---|---|---|
| 2,744,120 | 5/1956 | Fried et al. ........................ | 549/277 |
| 3,341,560 | 9/1967 | Campbell et al. ................ | 260/397.4 |
| 3,953,483 | 4/1976 | Hiraga et al. .................... | 260/397.4 |
| 4,235,893 | 11/1980 | Brodie et al. ...................... | 514/178 |

FOREIGN PATENT DOCUMENTS

| | | | |
|---|---|---|---|
| 105017 | 9/1964 | Norway ............................. | 260/397.4 |
| 929985 | 6/1963 | United Kingdom . | |

OTHER PUBLICATIONS

Bull et al., "An Unusual Acid-Catalyzed Reaction of Steroidal 4,6-Diols with Acetone", J. Chem. Soc.(D), 1971, (13), 717–718.
Brodie, "Overview of Recent . . . ", Cancer Research (Suppl.), 42, 3312s–33143s, Aug. (1982).
Covey et al., "A New Hypothesis Based . . . ", Cancer Reserach (Suppl.), 42 . . . 3327s–3333s, Aug. (1982).
U.S. Pat. No. 4,289,762, Derwent Publication.
U.S. Pat. No. 4,322,416, Derwent Publication.
Metcalf, et al., "Substrate-Induced . . . ", J. Am. Chem. Soc., 1981, 3321–3222.
EP 100,566A, Derwent Publication.
GB 2100-601 Derwent Publication.
100:968489. Chemical Abstracts, vol. 100, 1984.
Marsch, et al., "Aromatase Inhibitors. Synthesis . . . ", J. Med. Chem., 1985, 28, 788–795.
GB 2177-700-A Pharmaceuticals p. 3, Week 8704.
"Aromatase Inhibitors. Synthesis and Biological Activity of Androstenedione Derivatives", David A. Marsh et al., J. Med. Chem., 1985, pp. 788–795.

*Primary Examiner*—H. M. S. Sneed
*Assistant Examiner*—James Saba
*Attorney, Agent, or Firm*—Armstrong, Nikaido, Marmelstein & Kubovcik

[57] ABSTRACT

The invention relates to 4-substituted 6-alkylidenandrostene-3,17-dione derivatives of the following formula

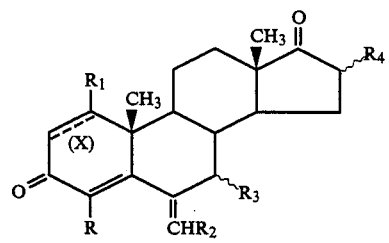

wherein each of $R_1$, $R_2$ and $R_3$ is, independently, hydrogen or $C_1$–$C_6$ alkyl; $R_4$ is hydrogen of fluorine; (x) represents a single or double bond; and R is, especially, a hydroxy or mercapto or amino group or a functional derivative thereof. The compounds of the invention show aromatase inhibitory activity and may be useful, for instance, in the treatment of hormone-dependent tumors and of prostatic hyperplasia.

5 Claims, No Drawings

4-SUBSTITUTED 6-ALKYLIDENANDROSTEINE-3,17-DIONE DERIVATIVES AND PROCESS FOR THEIR PREPARATION

The present invention relates to 4-substituted 6-alkylidenandrostene-3,17-dione derivatives, to a process for their preparation, to pharmaceutical compositions containing them, and to the use of said compounds for the treatment of hormone-dependent cancers. Basic and clinical data indicate that aromatized metabolites of androgens, i.e. the estrogens, are the hormones involved in the pathogenic cellular changes associated with the growth of some hormone-dependent cancers, e.g., breast, endometrial, ovarian and pancreatic carcinomas.

Estrogens are also involved in the pathogenesis of benign prostatic hyperplasia. Endogenous estrogens are ultimately formed from either androstenedione or testosterone as immediate precursors. The reaction of central importance is the aromatization of the steroidic ring A, which is performed by the enzyme aromatase. As aromatization is a unique reaction and the last in the series of steps in the biosynthesis of estrogens, it has been envisaged that an effective inhibition of the aromatase, resulting from compounds able to interact with the aromatizing steps, may have useful application for controlling the amount of circulating estrogens, estrogen-dependent processes in reproduction, and estrogen-dependent tumours. Known steroidal substances which have been reported to be endowed with an aromatase-inhibiting action are, for example, testololactone [U.S. Pat. No. 2,744,120], 4-hydroxy androst-4-ene-3,17-dione and esters thereof [see, for example, U.S. Pat. No. 4,235,893], 10-(1,2-propadienyl)estr-4-ene-3,17-dione [U.S. Pat. No. 4,289,762], 10-(2-propynyl)estr-4-ene-3,17-dione [J. Am. Chem. Soc., 103, 3221 (1981) and U.S. Pat. No. 4,322,416], 19-thioandrostene derivatives [Europ. Pat. Appl. No. 100566], androsta-4,6-diene-3,17-dione, androsta-1,4,6-triene-3,17-dione [G.B. Pat. Appl. No. 2,100,601A] and androsta-1,4-diene-3,17-dione [Cancer Res. (Suppl.) 42, 3327 (1982)].

The novel compounds of the present invention are potent aromatase inhibitors, by virtue of their ability to specifically inhibit estrogens synthesis.

The present invention provides compounds having the following general formula (I)

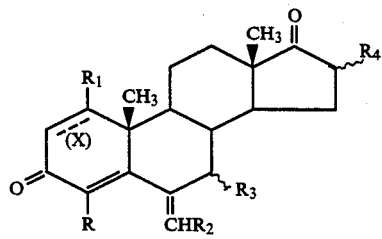 (I)

wherein
each of $R_1$, $R_2$ and $R_3$, independently, is hydrogen or $C_1$-$C_6$ alkyl; $R_4$ is hydrogen or fluorine;
the symbol ≡≡≡ indicates that (x) may be either a single bond or a double bond;
R is
(1) a group —$OR_5$ wherein $R_5$ is
  (a) hydrogen;
  (b) $C_1$-$C_6$ alkyl;
  (c) a phenyl or benzyl group, each unsubstituted or ring-substituted by one or more substituents chosen from $C_1$-$C_4$ alkyl, halogen, trifluoromethyl, nitro, amino, hydroxy and $C_1$-$C_4$ alkoxy;
  (d) a group —$COR_6$ wherein $R_6$ is
    (i) a $C_1$-$C_{22}$ saturated or $C_2$-$C_{22}$ unsaturated aliphatic hydrocarbon radical;
    (ii) a $C_4$-$C_7$ monocycloalkyl group; or
    (iii) a phenyl or benzyl group, each unsubstituted or ring substituted as reported above; or
  (e) a hydroxy protecting group;
(2) a group —$SR_7$ wherein $R_7$ either has one of the meanings
  (a) to (d) indicated above for $R_5$ or is a group —$SR_8$ wherein $R_8$ is
  (iv) $C_1$-$C_6$ alkyl;
  (v) a phenyl or benzyl group, each unsubstituted or ring-substituted as reported above; or
  (vi) a steroidic residue of formula

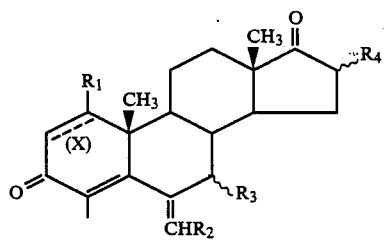

wherein $R_1$, $R_2$, $R_3$, $R_4$ and (x) are as defined above;
(3) the group —$N_3$; or
(4) a group

wherein each of $R_9$ and $R_{10}$, independently, is hydrogen or $C_1$-$C_6$ alkyl.

The invention includes also the pharmaceutically acceptable salts of the compounds of formula (I) containing a salifiable group.

In the formulae of this specification, a heavy solid line (—) indicates that a substituent is in the β-configuration, i.e. above the plane of the ring, and a wavy line (∿) indicates that a substituent, e.g., $R_3$ or $R_4$, may be either in the α-configuration, i.e. below the plane of the ring, or in the β-configuration or in both, i.e. a mixture thereof such as a racemic mixture. Also the 1-substituent $R_1$ may be, when (x) is a single bond, either in the α-configuration or in the β-configuration or in both, i.e. a mixture thereof such as a racemic mixture.

The formula reported above for the compounds of the invention is meant to comprise all the possible isomers of formula (I) both separately and in mixture, including also the Z and E isomers of the compounds of formula (I) in which $R_2$ is $C_1$-$C_6$ alkyl, both separately and in mixture.

The aliphatic hydrocarbon radicals, including the alkyl groups and the aliphatic moieties of the alkoxy groups, may be branched or straight chain. A $C_1$-$C_6$ or $C_1$-$C_4$ alkyl group is, preferably, methyl or ethyl.

A halogen is, preferably, chlorine, bromine or fluorine, in particular fluorine.

A $C_1$-$C_4$ alkoxy grou is, preferably, methoxy or ethoxy. A $C_1$-$C_{22}$ saturated aliphatic hydrocarbon radical is, preferably, a $C_1$-$C_{17}$ alkyl group, in particular, e.g., methyl, ethyl, n-propyl, n-butyl, tert-butyl or the residue of a saturated fatty acid, e.g. n-undecyl, n-tridecyl, n-pentadecyl or n-heptadecyl.

A $C_2$-$C_{22}$ unsaturated aliphatic hydrocarbon radical preferably contains 2 to 17 carbon atoms and, e.g., allyl, or the residue of an unsaturated fatty acid, e.g., cis- or trans-8-heptadecenyl.

A $C_4$-$C_7$ monocyloalkyl group is, preferably, a $C_5$-$C_7$ monocycloalkyl, in particular cyclopentyl or cyclohexyl.

A hydroxy protecting group is a group, especially an ether residue, which can be removed under mild reaction conditions, e.g. acid hydrolysis. Examples are residues of acetalic ethers, enolethers and silylethers. The preferred groups are:

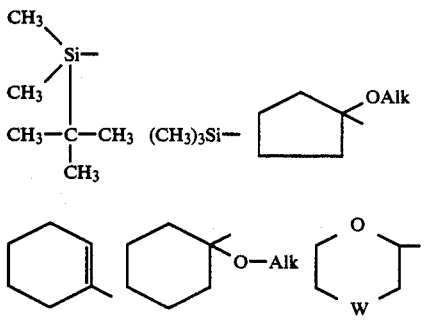

wherein W is —O— or —CH$_2$—, and Alk is a lower alkyl group; more preferably, they are 2'-tetrahydropyranyl or trimethylsylyl.

When R is a group —OR$_5$ or a group —SR$_7$ wherein R$_5$ or, respectively, R$_7$ is —COR$_6$, preferably R$_6$ is a $C_1$-$C_{22}$ saturated aliphatic hydrocarbon radical, especially a $C_1$-$C_{17}$ alkyl group and, in particular, one of those specified before, most preferably methyl or ethyl; or a phenyl or benzyl group either unsubstituted or ring-substituted by $C_1$-$C_4$ alkyl, in particular methyl, or by a fluorine, trifluoromethyl, nitro, hydroxy, methoxy or ethoxy group.

When R is a group —OR$_5$ or a group —SR$_7$, preferably R$_5$ or, respectively, R$_7$ is hydrogen; $C_1$-$C_6$ alkyl, in particular methyl or ethyl; or a group —COR$_6$ wherein R$_6$ is $C_1$-$C_{17}$ alkyl, in particular methyl or ethyl.

When R is a group

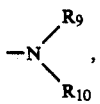

preferably each R$_9$ and R$_{10}$ is, independently, hydrogen or $C_1$-$C_3$ alkyl; preferred groups

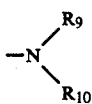

are amino, methylamino, ethylamino, dimethylamino and diethylamino; most preferably amino.

As already said, the invention includes also the pharmaceutically acceptable salts of the compounds of formula (I). Salts according to the invention are the salts of the compounds of formula (I) with pharmaceutically acceptable acids, both inorganic acids, e.g., hydrochloric, sulfuric or phosphoric acid, and organic acids such as, e.g., citric, fumaric, maleic, malic, ascorbic, tartaric, benzoic, acetic, phenylacetic, cyclohexylacetic, 3-cyclohexylpropionic, methanesulfonic, ethanesulfonic, benzenesulfonic, p-toluenesulfonic or p-nitrobenzenesulfonic acid. Also the quaternary ammonium salts and hydroxides of the compounds of the formula (I) wherein R is

are within the scope of the invention: they are, for instance, quaternary alkyl, e.g., methyl, ethyl or cetyl, ammonium salts, e.g. iodides, bromides or chlorides, or hydroxides.

A preferred class of compounds according to the invention are the compounds of formula (I) wherein each of R$_1$, R$_2$ and R$_3$, independently, is hydrogen or $C_1$-$C_6$ alkyl; R$_4$ is hydrogen or fluorine; (x) represents a single bond or a double bond; and R is a group —OR$_5$ or a group —SR$_7$ wherein R$_5$ or, respectively, R$_7$ is hydrogen, $C_1$-$C_6$ alkyl or a group —COR$_6$ wherein R$_6$ is $C_1$-$C_{17}$ alkyl.

In the above preferred class preferably R$_1$ is hydrogen or methyl; R$_2$ is hydrogen; R$_3$ is hydrogen, methyl or ethyl; and R$_4$ is hydrogen or fluorine; preferred values for R$_5$ and, respectively, R$_7$ are hydrogen, methyl, and ethyl; and preferred values for R$_6$ are methyl, ethyl, n-propyl, n-butyl and a residue of a saturated fatty acid, e.g., n-undecyl, n-tridecyl, n-pentadecyl or n-heptadecyl. When R$_1$ is a $C_1$-$C_6$ alkyl group, preferably (x) represents a double bond.

Example of specific compounds of the above preferred class are:
4-hydroxy-6-methylenandrost-4-ene-3,17-dione;
4-hydroxy-6-methylene-7α-methylandrost-4-ene-3,17-dione;
4-hydroxy-6-methylene-16α-fluoroandrost-4-ene-3,17-dione;
4-hydroxy-6-methylene-16β-fluoroandrost-4-ene-3,17-dione;
4-hydroxy-6-methylene-7α-methyl-16α-fluoroandrost-4-ene-3,17-dione;
4-hydroxy-6-methylene-7α-methyl-16β-fluoroandrost-4-ene-3,17-dione;
4-methoxy-6-methylenandrost-4-ene-3,17-dione;
4-methoxy-6-methylene-7α-methylandrost-4-ene-3,17-dione;
4-methoxy-6-methylene-16α-fluoroandrost-4-ene-3,17-dione;
4-methoxy-6-methylene-16β-fluoroandrost-4-ene-3,17-dione;
4-methoxy-6-methylene-7α-methyl-16α-fluoroandrost-4-ene-3,17-dione;
4-methoxy-6-methylene-7α-methyl-16β-fluoroandrost-4-ene-3,17-dione;
4-acetoxy-6-methylenandrost-4-ene-3,17-dione;

4-acetoxy-6-methylene-7α-methylandrost-4-ene-3,17-dione;
4-acetoxy-6-methylene-16α-fluoroandrost-4-ene-3,17-dione;
4-acetoxy-6-methylene-16β-fluoroandrost-4-ene-3,17-dione;
4-acetoxy-6-methylene-7α-methyl-16α-fluoroandrost-4-ene-3,17-dione;
4-acetoxy-6-methylene-7α-methyl-16β-fluoroandrost-4-ene-3,17-dione;
4-hydroxy-6-methylenandrosta-1,4-diene-3,17-dione;
4-hydroxy-6-methylene-7α-methylandrosta-1,4-diene-3,17-dione;
4-hydroxy-6-methylene-16α-fluoroandrosta-1,4-diene-3,17-dione;
4-hydroxy-6-methylene-16β-fluoroandrosta-1,4-diene-3,17-dione;
4-hydroxy-6-methylene-7α-methyl-16α-fluoroandrosta-1,4-diene-3,17-dione;
4-hydroxy-6-methylene-7α-methyl-16β-fluoroandrosta-1,4-diene-3,17-dione;
4-methoxy-6-methylenandrosta-1,4-diene-3,17-dione;
4-methoxy-6-methylene-7α-methylandrosta-1,4-diene-3,17-dione;
4-methoxy-6-methylene-16α-fluoroandrosta-1,4-diene-3,17-dione;
4-methoxy-6-methylene-16β-fluoroandrosta-1,4-diene-3,17-dione;
4-methoxy-6-methylene-7α-methyl-16α-fluoroandrosta-1,4-diene-3,17-dione;
4-methoxy-6-methylene-7α-methyl-16β-fluoroandrosta-1,4-diene-3,17-dione;
4-acetoxy-6-methylenandrosta-1,4-diene-3,17-dione;
4-acetoxy-6-methylene-7α-methylandrosta-1,4-diene-3,17-dione;
4-acetoxy-6-methylene-16α-fluoroandrosta-1,4-diene-3,17-dione;
4-acetoxy-6-methylene-16β-fluoroandrosta-1,4-diene-3,17-dione;
4-acetoxy-6-methylene-7α-methyl-16α-fluoroandrosta-1,4-diene-3,17-dione;
4-acetoxy-6-methylene-7α-methyl-16β-fluoroandrosta-1,4-diene-3,17-dione;
1-methyl-4-hydroxy-6-methylenandrosta-1,4-diene-3,17-dione;
1,7α-dimethyl-4-hydroxy-6-methylenandrosta-1,4-diene-3,17-dione;
1-methyl-4-hydroxy-6-methylene-16α-fluoroandrosta-1,4-diene-3,17-dione;
1-methyl-4-hydroxy-6-methylene-16β-fluoroandrosta-1,4-diene-3,17-dione;
1,7α-dimethyl-4-hydroxy-6-methylene-16α-fluoroandrosta-1,4-diene-3,17-dione;
1,7α-dimethyl-4-hydroxy-6-methylene-16β-fluoroandrosta-1,4-diene-3,17-dione;
1-methyl-4-methoxy-6-metylenandrosta-1,4-diene-3,17-dione;
1,7α-dimethyl-4-methoxy-6-methylenandrosta-1,4-diene-3,17-dione;
1-methyl-4-methoxy-6-methylene-16α-fluoroandrosta-1,4-diene-3,17-dione;
1-methyl-4-methoxy-6-methylene-16β-fluoroandrosta-1,4-diene-3,17-dione;
1,7α-dimethyl-4-methoxy-6-methylene-16α-fluorandrosta-1,4-diene-3,17-dione;
1,7α-dimethyl-4-methoxy-6-methylene-16β-fluorandrosta-1,4-diene-3,17-dione;
1-methyl-4-acetoxy-6-methylenandrosta-1,4-diene-3,17-dione;
1,7α-dimethyl-4-acetoxy-6-methylenandrosta-1,4-diene-3,17-dione;
1-methyl-4-acetoxy-6-methylene-16α-fluoroandrosta-1,4-diene-3,17-dione;
1-methyl-4-acetoxy-6-methylene-16β-fluoroandrosta-1,4-diene-3,17-dione;
1,7α-dimethyl-4-acetoxy-6-methylene-16α-fluoroandrosta-1,4-diene-3,17-dione;
1,7α-dimethyl-4-acetoxy-6-methylene-16β-fluoroandrosta-1,4-diene-3,17-dione;
4-mercapto-6-methylenandrost-4-ene-3,17-dione;
4-mercapto-6-methylene-7α-methylandrost-4-ene-3,17-dione;
4-mercapto-6-methylene-16α-fluoroandrost-4-ene-3,17-dione;
4-mercapto-6-methylene-16β-fluoroandrost-4-ene-3,17-dione;
4-mercapto-6-methylene-7α-methyl-16α-fluoroandrost-4-ene-3,17-dione;
4-mercapto-6-methylene-7α-methyl-16β-fluoroandrost-4-ene-3,17-dione;
4-acetylthio-6-methylenandrost-4-ene-3,17-dione;
4-acetylthio-6-methylene-7α-methylandrost-4-ene-3,17-dione;
4-acetylthio-6-methylene-16α-fluoroandrost-4-ene-3,17-dione;
4-acetylthio-6-methylene-16β-fluoroandrost-4-ene-3,17-dione;
4-acetylthio-6-methylene-7α-methyl-16α-fluoroandrost-4-ene-3,17-dione;
4-acetylthio-6-methylene-7α-methyl-16β-fluoroandrost-4-ene-3,17-dione;
4-ethylthio-6-methylenandrost-4-ene-3,17-dione;
4-ethylthio-6-methylene-7α-methylandrost-4-ene-3,17-dione;
4-ethylthio-6-methylene-16α-fluoroandrost-4-ene-3,17-dione;
4-ethylthio-6-methylene-16β-fluoroandrost-4-ene-3,17-dione;
4-ethylthio-6-methylene-7α-methyl-16α-fluoroandrost-4-ene-3,17-dione;
4-ethylthio-6-methylene-7α-methyl-16β-fluoroandrost-4-ene-3,17-dione;
4-mercapto-6-methylenandrosta-1,4-diene-3,17-dione;
4-mercapto-6-methylene-7α-methylandrosta-1,4-diene-3,17-dione;
4-mercapto-6-methylene-16α-fluoroandrosta-1,4-diene-3,17-dione;
4-mercapto-6-methylene-16β-fluoroandrosta-1,4-diene-3,17-dione;
4-mercapto-6-methylene-7α-methyl-16α-fluoroandrosta-1,4-diene-3,17-dione;
4-mercapto-6-methylene-7α-methyl-16β-fluoroandrosta-1,4-diene-3,17-dione;
4-acetylthio-6-methylenandrosta-1,4-diene-3,17-dione;
4-acetylthio-6-methylene-7α-methylandrosta-1,4-diene-3,17-dione;
4-acetylthio-6-methylene-16α-fluoroandrosta-1,4-diene-3,17-dione;
4-acetylthio-6-methylene-16β-fluoroandrosta-1,4-diene-3,17-dione;
4-acetylthio-6-methylene-7α-methyl-16α-fluoroandrosta-1,4-diene-3,17-dione;
4-acetylthio-6-methylene-7α-methyl-16β-fluoroandrosta-1,4-diene-3,17-dione;
4-ethylthio-6-methylenandrosta-1,4-diene-3,17-dione;

4-ethylthio-6-methylene-7α-methylandrosta-1,4-diene-3,17-dione;
4-ethylthio-6-methylene-16α-fluoroandrosta-1,4-diene-3,17-dione;
4-ethylthio-6-methylene-16β-fluoroandrosta-1,4-diene-3,17-dione;
4-ethylthio-6-methylene-7α-methyl-16α-fluoroandrosta-1,4-diene-3,17-dione;
4-ethylthio-6-methylene-7α-methyl-16β-fluoroandrosta-1,4-diene-3,17-dione;
1-methyl-4-mercapto-6-methylenandrosta-1,4-diene-3,17-dione;
1,7α-dimethyl-4-mercapto-6-methylenandrosta-1,4-diene-3,17-dione;
1-methyl-4-mercapto-6-methylene-16α-fluoroandrosta-1,4-diene-3,17-dione;
1-methyl-4-mercapto-6-methylene-16β-fluoroandrosta-1,4-diene-3,17-dione;
1,7α-dimethyl-4-mercapto-6-methylene-16α-fluoroandrosta-1,4-diene-3,17-dione;
1,7α-dimethyl-4-mercapto-6-methylene-16β-fluoroandrosta-1,4-diene-3,17-dione;
1-methyl-4-acetylthio-6-methylenandrosta-1,4-diene-3,17-dione;
1,7α-dimethyl-4-acetylthio-6-methylenandrosta-1,4-diene-3,17-dione;
1-methyl-4-acetylthio-6-methylene-16α-fluoroandrosta-1,4-diene-3,17-dione;
1-methyl-4-acetylthio-6-methylene-16β-fluoroandrosta-1,4-diene-3,17-dione;
1,7α-dimethyl-4-acetylthio-6-methylene-16α-fluoroandrosta-1,4-diene-3,17-dione;
1,7α-dimethyl-4-acetylthio-6-methylene-16β-fluoroandrosta-1,4-diene-3,17-dione;
1-methyl-4-ethylthio-6-methylenandrosta-1,4-diene-3,17-dione;
1,7α-dimethyl-4-ethylthio-6-methylenandrosta-1,4-diene-3,17-dione;
1-methyl-4-ethylthio-6-methylene-16α-fluoroandrosta-1,4-diene-3,17-dione;
1-methyl-4-ethylthio-6-methylene-16β-fluoroandrosta-1,4-diene-3,17-dione;
1,7α-dimethyl-4-ethylthio-6-methylene-16α-fluoroandrosta-1,4-diene-3,17-dione; and
1,7α-dimethyl-4-ethylthio-6-methylene-16β-fluoroandrosta-1,4-diene-3,17-dione.

Another preferred class of compounds according to the invention are the compounds of formula (I) wherein each of $R_1$, $R_2$ and $R_3$, independently, is hydrogen or $C_1$–$C_6$ alkyl;
$R_4$ is hydrogen or fluorine;
(x) represents a single bond or a double bond; and
R is a group

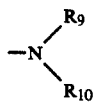

wherein one of $R_9$ and $R_{10}$ is hydrogen and the other is hydrogen or $C_1$–$C_6$ alkyl,
and the pharmaceutically acceptable salts thereof.

In the above preferred class, preferably $R_1$ is hydrogen or methyl; $R_2$ is hydrogen; $R_3$ is hydrogen, methyl or ethyl; and $R_4$ is hydrogen or fluorine; preferably one of $R_9$ and $R_{10}$ is hydrogen and the other is hydrogen, methyl or ethyl, a particularly preferred value for

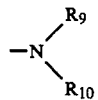

being amino.
When $R_1$ is $C_1$–$C_6$ alkyl, preferably (x) represents a double bond.
Examples of specific compounds of the above preferred class are:
4-amino-6-methylenandrost-4-ene-3,17-dione;
4-amino-6-methylene-7α-methylandrost-4-ene-3,17-dione;
4-amino-6-methylene-16α-fluoroandrost-4-ene-3,17-dione;
4-amino-6-methylene-16β-fluoroandrost-4-ene-3,17-dione;
4-amino-6-methylene-7α-methyl-16α-fluoroandrost-4-ene-3,17-dione;
4-amino-6-methylene-7α-methyl-16β-fluoroandrost-4-ene-3,17-dione;
4-amino-6-methylenandrosta-1,4-diene-3,17-dione;
4-amino-6-methylene-7α-methylandrosta-1,4-diene-3,17-dione;
4-amino-6-methylene-16α-fluoroandrosta-1,4-diene-3,17-dione;
4-amino-6-methylene-16β-fluoroandrosta-1,4-diene-3,17-dione;
4-amino-6-methylene-7α-methyl-16α-fluoroandrosta-1,4-diene-3,17-dione;
4-amino-6-methylene-7α-methyl-16β-fluoroandrosta-1,4-diene-3,17-dione;
1-methyl-4-amino-6-methylenandrosta-1,4-diene-3,17-dione;
1,7α-dimethyl-4-amino-6-methylenandrosta-1,4-diene-3,17-dione;
1-methyl-4-amino-6-methylene-16α-fluoroandrosta-1,4-diene-3,17-dione;
1-methyl-4-amino-6-methylene-16β-fluoroandrosta-1,4-diene-3,17-dione;
1,7α-dimethyl-4-amino-6-methylene-16α-fluoroandrosta-1,4-diene-3,17-dione;
1,7α-dimethyl-4-amino-6-methylene-16β-fluoroandrosta-1,4-diene-3,17-dione,
and the pharmaceutically acceptable salts thereof.

The compounds of the invention may be prepared by a process comprising:
(A) treating a compound of formula (II)

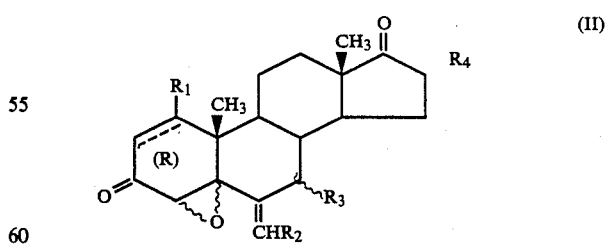

wherein $R_1$, $R_2$, $R_3$, $R_4$ and (x) are as defined above, by solvolysis such as to obtain a compound of formula (I) wherein R is a group —$OR_5$ wherein $R_5$ is hydrogen, $C_1$–$C_6$ alkyl or a phenyl or benzyl group unsubstituted or ring-substituted as defined above; or
(B) etherifying a compound of formula (I) wherein R is —OH such as to obtain a compound of formula (I)

wherein R is a group —OR$_5$ wherein R$_5$ is C$_1$–C$_6$ alkyl or a hydroxy protecting group; or (C) reacting a compound of formula (II) with a compound of formula (III)

R'$_7$—SH             (III)

wherein R'$_7$ is hydrogen, C$_1$–C$_6$ alkyl or a phenyl or benzyl group unsubstituted or ring-substituted as indicated above, so obtaining a compound of formula (I) wherein R is a group —SR$_7$ wherein R$_7$ either has one of the meanings reported above for R'$_7$ or is a group —SR$_8$ wherein R$_8$ is a steroidic residue as defined above under (vi) in which R$_1$, R$_2$, R$_3$, R$_4$ and (x) are the same as in the starting compound of formula (II); or (D) acylating a compound of formula (I) wherein R is —OH or respectively —SH, with a reagent carrying a —COR$_6$ moiety, wherein R$_6$ is as defined above, so obtaining a compound of formula (I) wherein R is a group —OR$_5$ or, respectively, a group —SR$_7$ wherein R$_5$ and, respectively, R$_7$ are a group —COR$_6$ wherein R$_6$ is as defined above, or (E) reacting a compound of formula (I) wherein R is —SH with a compound of formula (IV)

R$_8$—SH             (IV)

wherein R$_8$ is a defined above, so obtaining a compound of formula (I) wherein R is —SR$_7$ wherein R$_7$ is a group —SR$_8$ in which R$_8$ is as defined above; or (F) reacting a compound of formula (II) with a compound of formula (V)

M—N$_3$             (V)

wherein M is an alkali metal or ammonium cation or a tri-C$_1$–C$_6$-alkylsilyl group, so obtaining a compound of formula (I) wherein R is the group —N$_3$; or (G) reducing a compound of formula (I) wherein R is the group —N$_3$, so obtaining a compound of formula (I) wherein R is a group

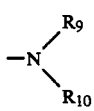

wherein R$_9$ and R$_{10}$ are both hydrogen; or (H) alkylating a compound of formula (I) wherein R is a group

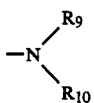

wherein R$_9$ and R$_{10}$ are both hydrogen, so obtaining a compound of formula (I) wherein R is a group

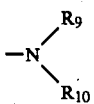

wherein at least one of R$_9$ and R$_{10}$ is C$_1$–C$_6$ alkyl; and, if desired, salifying a compound of formula (I) containing a salifiable group or obtaining a free compound from a salt and/or, if desired, separating a mixture of isomers of formula (I) into the single isomers.

The solvolysis of a compound of formula (II) in order to obtain a compound of formula (I) wherein R is a group —OR$_5$ wherein R$_5$ is hydrogen may be carried out, e.g., by treatment with suitable mineral acids, e.g., sulfuric acid, hydrochloric acid, phosphoric acid, acetic acid, or a mixture thereof, at a temperature ranging from about the room temperature to about the reflux temperature. Preferably the reaction is carried out by treatment with a mixture of glacial acetic acid and concentrated sulfuric acid, at a temperature ranging from about 10° C. to about 50° C., e.g., according to B. Camerino et al., 1956, Il Farmaco 7, 19.

The solvolysis of a compound of formula (II) in order to obtain a compound of a formula (I) wherein R is a group —OR$_5$ wherein R$_5$ is C$_1$–C$_6$ alkyl, may be, e.g., carried out by treatment with a suitable C$_1$–C$_6$ alkyl-alcohol in aqueous solution, in the presence of an alkali which is, preferably, an alkali metal, e.g., sodium or potassium, hydroxide, at a temperature ranging, e.g., from about 20° C. to the reflux temperature, for reaction times varying, e.g., from about 1 hour to about 48 hours, for instance according to B. Camerino et al., 1962, Gazz. Chim. It. 92, 709.

In similar way, solvolysing the compound (II) with the appropriate phenol derivative or benzyl alcohol derivative, a compound (I) wherein R is a group —OR$_5$ in which R$_5$ is a phenyl or benzyl group either unsubstituted or ring-substituted as indicated above, may be obtained. The etherification of a compound of formula (I) wherein R is —OH to give a compound of formula (I) wherein R is a group —OR$_5$ wherein R$_5$ is C$_1$–C$_6$ alkyl or a hydroxy protecting group, may be carried out by the usual procedures described in the organic chemistry for converting alcohol into ethers; for instance C$_1$–C$_6$ alkyl ethers may be obtained by reaction with the appropriate diazoalkane or C$_1$–C$_6$ alkyl halide under standard conditions, and, e.g., silyl ethers may be prepared by reaction with the appropriate silyl halide in the presence of a base, again using conventional procedures.

The reaction between a compound of formula (II) and a compound of formula (III) wherein R$_7$' is hydrogen (i.e. hydrogen sulfide) leading, by oxirane ring cleavage, to a compound of formula (I) wherein R is a group —SR$_7$ wherein R$_7$ is hydrogen may be carried out in presence of a base, either organic such as, for instance, pyridine or a tri-C$_1$–C$_6$-alkylamine e.g. triethylamine, or inorganic such as, e.g., NaOH or KOH, operating in an inert solvent, such as, for example, methanol, ethanol, water, dioxane or dimethoxyethane, and under inert atmosphere.

When the reaction is carried out under air or oxygen atmosphere, the dimeric disulfide is obtained, i.e. the compound of formula (I) wherein R is —SR$_7$ with R$_7$ being a group —SR$_8$ in which R$_8$ is a steroidic residue as defined above under (vi) having for R$_1$, R$_2$, R$_3$, R$_4$ and (x) the same meanings as the starting compound of formula (II).

The reaction between a compound of formula (II) and a compound of formula (III) wherein R'$_7$ is C$_1$–C$_6$ alkyl or a phenyl or benzyl group as defined above leading, by oxirane ring cleavage, to a compound of formula (I) wherein R is a group —SR$_7$ wherein R$_7$ is C$_1$–C$_6$ alkyl or a phenyl or benzyl group as defined above, may be carried out in presence of an acid such as, for example, polyphosphoric acid, operating in an inert solvent which may be, for instance, dioxane, dimethoxyethane, water, methanol or ethanol at a temperature between about 0° C. and about 50° C. The acylation of a compound of formula (I) wherein R is —OH or, respectively, —SH, in order to obtain a compound of formula (I) wherein R is a group —OR$_5$ or, respectively, a group —SR$_7$ wherein R$_5$ and, respectively, R$_7$ are a group —COR$_6$ wherein R$_6$ is as defined above, may be performed by reaction with a suitable acylating agent carrying the —COR$_6$ moiety, which may be, for example, a reactive derivative of the appropriate carboxylic acid, e.g., a halide, preferably the chloride or the anhydride or a mixed anhydride, thereof, in the presence of a basic agent, preferably an organic base, such as, e.g., pyridine. The reaction between a compound of formula (I), wherein R is —SH and a compound of formula (IV), in order to obtain a compound of formula (I) wherein R is a group —SR$_7$ wherein R$_7$ is —SR$_8$ with R$_8$ as defined above, may be performed according to known methods for the formation of disulfides, e.g. as described in Comprehensive Organic Chemistry, Vol. 3, pag. 283–6, Pergamon Press.

When M in the compound (V) is an alkali metal, this is, preferably, sodium, potassium ot lithium; when M is a tri-C$_1$-C$_6$ alkyl silyl group, this is, preferably, trimethylsilyl or dimethyl-tert.butylsilyl.

Preferred compounds (V) are sodium azide, lithium azide, trimethylsilyl azide and dimethyl tert.butyl silyl azide. The reaction between a compound of formula (II) and a compound of formula (V) is preferably carried out in a dipolar aprotic solvent such as, for instance, N,N-dimethylformamide or dimethylsulfoxide; some water or an aqueous alcoholic, e.g. methanolic or ethanolic, solution may be added, if desired, to increase the solubility of the azide (V). The reaction temperature, e.g., from about 0° C. to about 60° C. Some acid, e.g. sulfuric acid may be added, if desired, to increase the reactivity of the oxirane ring.

The reduction of a compound of formula (I) wherein R is the group —N$_3$ in order to obtain a compound of formula (I) wherein R is a group

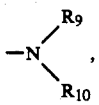

wherein R$_9$ and R$_{10}$ are both hydrogen, may be carried out following known methods, for instance, with a variety of reducing agents, e.g. propane-1,3-dithiol in triethylamine, as described in Tetr. Lett., 39, 3633 (1978); dithiolthreitol in aqueous solutions; mercaptoacetic acid and triethylamine; or, for instance, triphenylphosphine in tetrahydrofuran and aqueous solution, as described, e.g., in Bull. Soc. Chim. Fr., 1985, 815.

The alkylation of a compound of formula (I) wherein R is a group

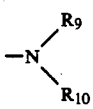

wherein R$_9$ and R$_{10}$ are both hydrogen to obtain a corresponding compound of formula (I) wherein R is a group

wherein at least one of R$_9$ and R$_{10}$ is C$_1$-C$_6$ alkyl, may be carried out by reaction with a suitable alkylating agent which, e.g., a C$_1$-C$_6$ alkyl halide, in particular iodide, or di-C$_1$-C$_6$-alkyl-sulfate; for obtaining a compound of formula (I) wherein R is a group

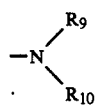

wherein at least one of R$_9$ and R$_{10}$ is methyl or ethyl suitable alkylating agents are, e.g., methyl iodite, dimethylsulfate or, respectively, ethyliodide and diethylsulfate. Reaction conditions well known to the skilled in the art and well described in the organic chemistry may be followed: see, e.g., Lucier et al., Org. Synth. 44, 72 (1964).

A compound of formula (II) wherein (x) is single bond and R$_1$, R$_2$, R$_3$ and R$_4$ are as defined above may be prepared by epoxidation of a compound of formula (VI)

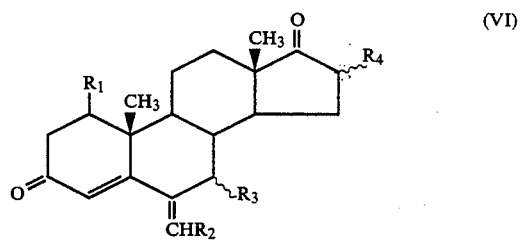

wherein R$_1$, R$_2$, R$_3$ and R$_4$ are as defined above. The epoxidation may be carried out by treatment with a suitable oxidizing agent which may be, for instance, concentrated, e.g. 36%, hydrogen peroxide in an alcoholic alkali-metal hydroxide solution, preferably KOH or NaOH in methanol, at a temperature ranging e.g., approximately, from 0° C. to 25° C. for a time of from about 2 hrs to several days.

A compound of formula (II) wherein (x) is a double bond and R$_1$, R$_2$, R$_3$ and R$_4$ are as defined above, may be prepared by dehydrogenating a corresponding compound of formula (II) wherein (x) is a single bond, following known methods, e.g. by treatment with 2,3-dichloro-5,6-dicyano benzoquinone as reported, e.g., by D. Walker and J. D. Hiebert in Chem. Rev. 67, 153 (1967) or with selenium dioxide, chloranil or benzeneseleninic anhydride. Preferably the said reaction is performed with benzeneseleninic anhydride in an inert solvent, e.g., chlorobenzene or carbon tetrachloride, at a temperature ranging, e.g., from about 60° C. to about 120° C. and for reaction times between about two hours and about 48 hours.

A compound of formula (VI) may be in its turn obtained by alkylidenation of a compound of formula (VII)

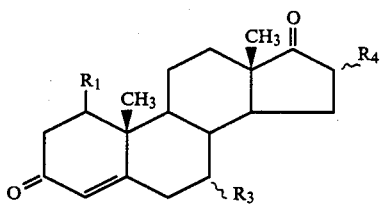

(VII)

wherein R₁, R₃ and R₄ are as defined above, according to known methods, e.g. according to the method of K. Annen, Synthesis, 34 (1982). Preferably a compound of formula (VII) is reacted with an unsubstituted or appropriately $C_1$-$C_6$ alkyl substituted formaldehyde diethylacetal in refluxing chloroform in the presence of phosphoryl chloride and sodium acetate. Alternatively, the same reaction may be carried out in other inert solvents, e.g. 1,2-dichloroethane, diethyl ether or dioxane, and in the presence of other suitable condensing agents, e.g., phosphorous pentoxide or p-toluenesulphonic acid.

The compounds of formula (VII) wherein R₃ is hydrogen are known compounds, or comppounds that can be prepared by known methods from known compounds.

The compounds of formula (VII) wherein R₃ is $C_1$-$C_6$ alkyl, e.g., obtained by alkylation of a compound of formula (VIII)

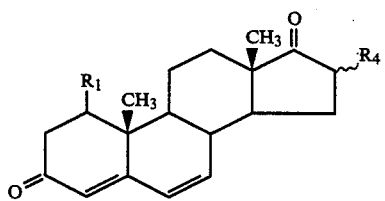

(VIII)

wherein R and R₄ are as defined above, according to known methods. For instance, alkyl lithium or alkyl magnesium halides are reacted with a copper (I) halide, e.g. iodide, in an ethereal solvent, e.g. diethyl ether, at 0° C.-10° C., to form the alkyl copper complex, which is then added to a solution of the compound (VIII) in a suitable solvent, e.g. diethyl ether or tetrahydrofuran, at a temperature ranging from about 0° C. to about 50° C.

The compound of formula (VIII), wherein R₁ and R₄ are both hydrogen is a known, commercially available compound. The compounds of formula (VIII) wherein R₁ and/or R₄ are different from hydrogen, e.g., obtained by dehydrogenation of a corresponding compound of formula (VII) wherein R₃ is hydrogen, according to known methods.

In particular, the compounds of formula (VII) and (VIII) wherein R₄ is fluorine may be prepared form the corresponding compounds of formula (VII) and (VIII) wherein R₄ is hydrogen by known methods, for instance by the process described by J. A. Katzenellenbogen et al., in J. Org. Chem., 49, 4900 (1984).

The compounds of the present invention are inhibitors of the biotransformation of androgens into estrogens, i.e., they are steroidal aromatase inhibitors. The aromatase inhibitory activity of these compounds is shown, e.g., by the fact that they are active in the in vitro test described by Thompson and Siiteri (E. A. Thompson and P. K. Siiteri, J. Boil. Chem. 249, 5364, 1974) which utilizes the human placental microsomal fraction as enzyme source. In this test the aromatization rate of androstenedione into estrone was evaluated by incubating [1β,2β-³H]androstenedione (50 nM) in the presence of NADPH with the enzyme preparation and by measuring the amount of ³H₂O formed during 20 min incubation at 37° C.

By virtue of their ability to inhibit aromatase and, consequently, to reduce estrogen levels, the new compounds of the invention may be useful in the treatment and prevention of various estrogen dependent diseases, e.g., breast, endometrial, ovarian and pancreatic cancers, gynecomastia, benign breast disease, endometriosis, polycystic ovarian disease and precocious puberty. Another application of the compounds of the invention may be in the therapeutic and/or prophylactic treatment of prostatic hyperplasia, a disease of the estrogen dependent stromal tissue. The new compounds can find also use for the treatment of male infertility associated with oligospermia and for female fertility control, by virtue of their ability to inhibit ovulation and egg nidation.

In view of their high therapeutic index, the compounds of the invention can be used safely in medicine. For example, the approximate acute toxicity ($LD_{50}$) of the compounds of the invention in the mouse, determined by single administration of increasing doses and measured on the seventh day after the treatment was found to be negligible.

The compounds of the invention can be administered in a variety of dosage forms, e.g. orally, in the form of tablets, capsules, sugar of film coated tablets, liquid solutions or suspensions; rectally, in the form of suppositories; parenterally, e.g. intramuscularly, or by intravenous injection of infusion; or topically.

The dosage depends on the age, weight, conditions of the patient and administration route; for example the dosage adopted for oral administration to adult humans may range from about 10 to about 150-200 mg pro dose, from 1 to 5 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate; and/or polyethylene glycols; binding agents, e.g. starches, arabic gums, gelatin, methylcellulose, carboxymethylcellulose or polyvinyl pyrrolidone; di-saggregating agents, e.g. a starch, alginic acid, alginates or sodium starch glycolate; effervescing mixtures; dyestuff; sweeteners; wetting agents, such as lecithin, polysorbates, laurysulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration e.g. syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alignate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusione may contain as carrier, for example, sterile water or, preferably, they may be in the form of sterile, aqueous, isotonic saline solutions. The suppositories may contain together with the active compound a pharmaceutically acceptable carrier, e.g. cocoa-butter, polyethylene glycol, a polyoxyethylene sorbitan fatty acid ester surfactant or lecithin. Compositions for topical application, e.g., creams, lotions or pastes, e.g., prepared by admixing the active ingredient, with a conventional oleaginous or emulsifying excipient.

The following examples illustrate but do not limit the invention.

EXAMPLE I 6-methylenandrost-4-ene-3,17-dione (VI, $R_1=R_2=R_3=R_4=H$, (x)=single bond)

A mixture of androst-4-ene-3,17-dione (32 g, 111 mmole), formaldehyde diethylacetal (620 ml), phosphorus oxychloride (78.6 ml, 827 mmole), anhydrous sodium acetate (20.7 g, 252 mmole) and chloroform (1150 ml) is stirred and refluxed during 5 hrs. To the cooled reaction mixture is added dropwise, and in the order, a 40% potassium carbonate aqueous solution (800 ml) and a 2N sodium hydroxide aqueous solution (1320 ml) under vigorous stirring. After 1 hour of additional stirring, the organic phase is separated and the aqueous phase is extracted with two portions of chloroform (300 ml+200 ml). The combined organic phases are washed with water, dried over anhydrous calcium chloride, filtered and evaporated in vacuo. The resulting residue is column chromatographed over silica gel. Elution with n-hexane: ethyl acetate 80:20 yields a solid (20 g) which is crystallised from isopropyl ether (240 ml). There are obtained 14 g (42% yield) of the title compound, m.p. 155°–60° C.

In analogous fashion and starting from the appropriate precursors of formula (VII) the following compounds can be prepared:
6-methylene-7α-methylandrost-4-ene-3,17-dione;
6-methylene-16α-fluoroandrost-4-ene-3,17-dione;
6-methylene-16β-fluoroandrost-4-ene-3,17-dione;
6-methylene-7α-methyl-16α-fluoroandrost-4-ene-3,17-dione;
6-methylene-7α-methyl-16β-fluoroandrost-4-ene-3,17-dione;
1β-methyl-6-methylenandrost-4-ene-3,17-dione;
1β,7α-dimethyl-6-methylenandrost-4-ene-3,17-dione;
1β-methyl-6-methylene-16α-fluoroandrost-4-ene-3,17-dione;
1β-methyl-6-methylene-16β-fluoroandrost-4-ene-3,17-dione;
1β,7α-dimethyl-6-methylene-16α-fluoroandrost-4-ene-3,17-dione; and
1β,7α-dimethyl-6-methylene-16β-fluoroandrost-4-ene-3,17-dione.

EXAMPLE II 4,5-epoxy-6-methylenandrostane-3,17 dione (II, $R_1=R_2=R_3=R_4=H$, (x)=single bond)

To a solution of 6-methylenandrost-4-ene-3,17-dione (5 g, 16.7 mmole) in methanol (200 ml) cooled at 0° C. is added a cold 36% hydrogen peroxide solution (17 ml) and a cold 2% sodium hydroxide aqueous solution. The resulting reaction mixture is stirred at 0°–5° C. during 24 hrs, then it is poured into iced water (1400 ml) with vigorous stirring. The resulting precipitate is filtered, washed with water and dried in vacuo. There are obtained 4.2 g (80% yield) of the title compound, NMR (CDCl$_3$, δ): 0.90 (3H, s), 0.07 (3H, s), 3.52 (1H, s), 4.92 (1H, br s), 5.06 (1H, br s).

In analogous fashion and starting from the appropriate precursors of formula (VI) the following compounds can be prepared:
4,5-epoxy-6-methylene-7α-methylandrostane-3,17-dione;
4,5-epoxy-6-methylene-16α-fluoroandrostane-1,17-dione;
4,5-epoxy-6-methylene-16β-fluoroandrostane-3,17-dione;
4,5-epoxy-6-methylene-7α-methyl-16α-fluoroandrostane-3,17-dione;
4,5-epoxy-6-methylene-7α-methyl-16β-fluoroandrostane-3,17-dione;
4,5-epoxy-1β-methyl-6-methylenandrostane-3,17-dione;
4,5-epoxy-1β,7α-dimethyl-6-methylenandrostane-3,17-dione;
4,5-epoxy-1β-methyl-6-methylene-16α-fluoroandrostane-3,17-dione;
4,5-epoxy-1β-methyl-6-methylene-16β-fluoroandrostane-3,17-dione;
4,5-epoxy-1β,7α-dimethyl-6-methylene-16α-fluoroandrostane-3,17-dione; and
4,5-epoxy-1β,7α-dimethyl-6-methylene-16β-fluoroandrostane-3,17-dione.

EXAMPLE III 4,5-epoxy-6-methyleandrost-1-ene-3,17-done (II, $R_1=R_2=R_3=R_4=H$, (x)=double bond)

A mixture of 4,5-epoxy-6-methylenandrostane-3,17-dione (3 g, 9.6 mmole) and dichlorodicyanobenzoquinone (1.7 g) dissolved in dixoane (60 ml) are refluxed during 15 hrs. The cooled reaction mixture is filtered through alumina and the filtrate is evaporated in vacuo. The resulting residue is taken up with ethyl acetate, washed with water and dried over sodium sulfate. The resulting solution is filtered and evaporated in vacuo to yield a crude product which is purified by column chromatography on silica gel eluting with a 10–40% gradient of ethyl acetate in n-hexane. There are obtained 1.5 g (51% yield) of the title compound, NMR (CDCl$_3$, δ): 0.93 (3H, s), 1.13 (3H, s), 3.71 (1H, d), 5.03 (2H, m), 5.86 (1H, d), 6.78 (1H, d).

In analogous fashion and starting from the appropriate precursors of formula (II) wherein (x) is a single bond, the following compounds can be prepared:
4,5-epoxy-6-methylene-7α-methylandrost-1-ene-3,17-dione;
4,5-epoxy-6-methylene-16α-fluoroandrost-1-ene-3,17-dione;
4,5-epoxy-6-methylene-16β-fluoroandrost-1-ene-3,17-dione;

4,5-epoxy-6-methylene-7α-methyl-16α-fluoroandrost-1-ene-3,17-dione;

4,5-epoxy-6-methylene-7α-methyl-16β-fluoroandrost-1-ene-3,17-dione;

4,5-epoxy-1-methyl-6-methylenandrost-1-ene-3,17-dione;

4,5-epoxy-1,7α-dimethyl-6-methylenandrost-1-ene-3,17-dione;

4,5-epoxy-1-methyl-6-methylene-16α-fluoroandrost-1-ene-3,17-dione;

4,5-epoxy-1-methyl-6-methylene-16β-fluoroandrost-1-ene-3,17-dione;

4,5-epoxy-1,7α-dimethyl-6-methylene-16α-fluoroandrost-1-ene-3,17-dione; and 4,5-epoxy-1,7α-dimethyl-6-methylene-16β-fluoroandrost-1-ene-3,17-dione.

EXAMPLE IV 4-hydroxy-6-methylenandrost-4-ene-3,17-dione (I, R=—OH, $R_1=R_2=R_3=R_4$=H, (x)=single bond)

4,5-epoxy-6-methylenandrostane-3,17-dione (3.6 g, 11.5 mmole) is added portionwise to a stirred cooled mixture of glacial acetic acid (98 ml) and conc. sulfuric acid (2 ml). The resulting reaction mixture is stirred at 0°–5° C. during 24 hrs. and then poured into a mixture of ice and water (900 g). The resulting precipitate is filtered off, dried and purified by column chromatography on silica gel eluting with methylene chloride: ethyl acetate 95:5. There are obtained 1.08 g (30% yield) of the title compound.

Elemental analysis: calculated % (found %): C 76.40, (76.30). H 8.34, (8.29).

NMR (CDCl$_3$, δ): 0.91 (3H, s), 1.13 (3H, s), 5.10 (1H, dd), 5.28 (1H, dd), 6.1 (1H, s).

In analogous fashion and starting from the appropriate precursors of formula (II) the following compounds can be prepared:

4-hydroxy-6-methylene-7α-methylandrost-4-ene-3,17-dione;

4-hydroxy-6-methylene-16α-fluoroandrost-4-ene-3,17-dione;

4-hydroxy-6-methylene-16β-fluoroandrost-4-ene-3,17-dione;

4-hydroxy-6-methylene-7α-methyl-16α-fluoroandrost-4-ene-3,17-dione;

4-hydroxy-6-methylene-7α-methyl-16β-fluoroandrost-4-ene-3,17-dione;

4-hydroxy-6-methylenandrosta-1,4-diene-3,17-dione;

4-hydroxy-6-methylene-7α-methylandrosta-1,4-diene-3,17-dione;

4-hydroxy-6-methylene-16α-fluoroandrosta-1,4-diene-3,17-dione;

4-hydroxy-6-methylene-16β-fluoroandrosta-1,4-diene-3,17-dione;

4-hydroxy-6-methylene-7α-methyl-16α-fluoroandrosta-1,4-diene-3,17-dione;

4-hydroxy-6-methylene-7α-methyl-16β-fluoroandrosta-1,4-diene-3,17-dione;

1-methyl-4-hydroxy-6-methylenandrosta-1,4-diene-3,17-dione;

1,7α-dimethyl-4-hydroxy-6-methylenandrosta-1,4-diene-3,17-dione;

1-methyl-4-hydroxy-6-methylene-16α-fluoroandrosta-1,4-diene-3,17-dione;

1-methyl-4-hydroxy-6-methylene-16β-fluoroandrosta-1,4-diene-3,17-dione;

1,7α-dimethyl-4-hydroxy-6-methylene-16α-fluoroandrosta-1,4-diene-3,17-dione; and 1,7α-dimethyl-4-hydroxy-6-methylene-16β-fluoroandrosta-1,4-diene-3,17-dione.

EXAMPLE V 4-methoxy-6-methylenandrost-4-ene-3,17-dione (I, R=OCH$_3$, $R_1=R_2=R_3=R_4$=H, (x)=single bond)

To a stirred suspension of 4,5-epoxy-6-methylenandrostane-3,17-dione (0.630 g, 2 mmole) in methanol (63 ml) is added a 4N sodium hydroxide aqueous solution (6.3 ml). The resulting mixture is refluxed for 1 hr, cooled to room temperature, evaporated in vacuo, taken up with water, neutralised with a 37% hydrochloric acid solution and kept at 0°–5° C. overnight. The resulting precipitate is filtered off, washed with water, dried and purified by flash column chromatography on silica gel eluting with n-hexane: ethyl acetate 60:40. There are obtained 0.530 g (75% yield) of the title compound, m.p. 196°–198° C.

Elemental analysis: Calculated % (found %): C 76.83 (76.14). H 8.54 (8.60).

NMR (CDCl$_3$, δ) 0.90 (3H, s), 1.14 (3H, s), 3.60 (3H, s), 5.10 (1H, dd). 5.30 (1H, dd).

In analogous fashion and starting from the appropriate precursors of formula (II) the following compounds can be prepared:

4-methoxy-6-methylene-7α-methylandrost-4-ene-3,17-dione;

4-methoxy-6-methylene-16α-fluoroandrost-4-ene-3,17-dione;

4-methoxy-6-methylene-16β-fluoroandrost-4-ene-3,17-dione;

4-methoxy-6-methylene-7α-methyl-16α-fluoroandrost-4-ene-3,17-dione;

4-methoxy-6-methylene-7α-methyl-16β-fluoroandrost-4-ene-3,17-dione;

4-methoxy-6-methylenandrosta-1,4-diene-3,17-dione;

4-methoxy-6-methylene-7α-methylandrosta-1,4-diene-3,17-dione;

4-methoxy-6-methylene-16α-fluoroandrosta-1,4-diene-3,17-dione;

4-methoxy-6-methylene-16β-fluoroandrosta-1,4-diene-3,17-dione;

4-methoxy-6-methylene-7α-methyl-16α-fluoroandrosta-1,4-diene-3,17-dione;

4-methoxy-6-methylene-7α-methyl-16β-fluoroandrosta-1,4-diene-3,17-dione;

1-methyl-4-methoxy-6-methylenandrosta-1,4-diene-3,17-dione;

1,7α-dimethyl-4-methoxy-6-methylenandrosta-1,4-diene-3,17-dione;

1-methyl-4-methoxy-6-methylene-16α-fluoroandrosta-1,4-diene-3,17-dione;

1-methyl-4-methoxy-6-methylene-16β-fluoroandrosta-1,4-diene-3,17-dione;

1,7α-dimethyl-4-methoxy-6-methylene-16α-fluoroandrosta-1,4-diene-3,17-dione and 1,7α-dimethyl-4-methoxy-6-methylene-16β-fluoroandrosta-1,4-diene-3,17-dione.

EXAMPLE VI 4-amino-6-methylenandrost-4-ene-3,17-dione (I, R=NH$_2$, $R_1=R_2=R_3=R_4$=H, (x)=single bond)

To a stirred solution of 4,5-epoxy-6-methylenandrostane-3,17-dione (0.39 g, 1.25 mmole) in dry dimethylsulfoxide (8 ml) is added conc. sulfuric acid (0.1 ml) and sodium azide (1.5 g). The resulting reaction mixture is heated at about 100° C. during 15 min., cooled, poured into a mixture of water (50 ml) and conc. hydrochloric acid (4 ml), and extracted with ethyl acetate (3×50 ml).

The combined organic extracts are dried over sodium sulfate, filtered and evaporated in vacuo to yield a solid which is purified by flash column chromatography eluting with n-hexane: ethyl acetate 1:1. There are obtained 0.16 g of 4-azido-6-methylenandrost-4-ene-3,17-dione (I, R=N$_3$) which are dissolved in tetrahydrofuran (2 ml) and treated by the portionwise addition of triphenyl phosphine (0.2 g) at room temperature, followed by the addition of water (0.5 ml). The resulting reaction mixture is heated at reflux for 24 hrs, cooled, diluted by the additon of a 1N HCl aqueous solution (50 ml) and washed with methylene chloride (2×50 ml) which is discarded. The aqueous phase is adjusted to pH 10 and extracted with methylene chloride (3×50 ml). The combined organic extracts are washed with brine, dried over sodium sulfate and evaporated in vacuo. The resulting residue is purified by flash column chromatography eluting with n-hexane: diethyl ether 1:2. There are obtained 0.13 g (80% yield) of the title compound.

Elemental analysis: Calculated % (found %): C 76.68 (76.51). H 8.63 (8.70). N 4.47 (4.52).

NMR (CDCl$_3$, δ): 0.91 (3H, s), 1.13 (3H, s), 3.00 (2H, br s), 5.11 (1H, dd), 5.30 (1H, dd).

In analogous fashion and starting from the appropriate precursors of formula (II) the following compounds can be prepared:
4-amino-6-methylene-7α-methylandrost-4-ene-3,17-dione;
4-amino-6-methylene-16α-fluoroandrost-4-ene-3,17-dione;
4-amino-6-methylene-16β-fluoroandrost-4-ene-3,17-dione;
4-amino-6-methylene-7α-methyl-16α-fluoroandrost-4-ene-3,17-dione;
4-amino-6-methylene-7α-methyl-16β-fluoroandrost-4-ene-3,17-dione;
4-amino-6-methylenandrosta-1,4-diene-3,17-dione;
4-amino-6-methylene-7α-methylandrosta-1,4-diene-3,17-dione;
4-amino-6-methylene-16α-fluoroandrosta-1,4-diene-3,17-dione;
4-amino--methylene-16β-fluoroandrosta-1,4-diene-3,17-dione;
4-amino-6-methylene-7α-methyl-16α-fluoroandrosta-1,4-diene-3,17-dione;
4-amino-6-methylene-7α-methyl-16β-fluoroandrosta-1,4-diene-3, 17-dione;
1-methyl-4-amino-6-methylenandrosta-1,4-diene-3,17-dione;
1,7α-dimethyl-4-amino-6-methylenandrosta-1,4-diene-3,17-dione;
1-methyl-4-amino-6-methylene-16α-fluoroandrosta-1,4-diene-3,17-dione;
1-methyl-4-amino-6-methylene-16β-fluoroandrosta-1,4-diene-3,17-dione;
1,7α-dimethyl-4-amino-6-methylene-16α-fluoroandrosta-1,4-diene-3,17-dione; and
1,7α-dimethyl-4-amino-6-methylene-16β-fluoroandrosta-1,4-diene-3,17-dione.

EXAMPLE VII 4-mercapto-6-methylenandrost-4-ene-3,17-dione (I, R=—SH, R$_1$=R$_2$=R$_3$=R$_4$=H, (x)=single bond)

To a stirred solution of 4,5-epoxy-6-methylenandrostane-3,17-dione (0.40 g, 1.25 mmole) in dioxane (12 ml) and ethanol (12 ml) is added a solution of technical sodium hydrosulfide (0.55 g) in ethanol (25 ml) dropwise under nitrogen at 10° C. The resulting reaction mixture is stirred at room temperature for 1 hour, neutralised with glacial acetic acid (1 ml) and extracted with chloroform (50 ml). The organic extract is washed with water, a saturated NaHCO$_3$ aqueous solution, water, and then dried over sodium sulfate. The solvent is evaporated in vacuo and the crude product is column chromatographed over silica gel eluting with benzene. There are obtained 0.227 g (55%) of the title compound, m.p. 195°-7° C., Elemental analysis: Calculated % (found %): C 72.72 (72.64). H 7.87 (7.95). S 9.69 (9.50).

I.R. (KBr, cm$^{-1}$): 2560, 1730, 1660, 1560.

In analogous fashion and starting from the appropriate precursors of formula (II), the following compounds can be prepared:
4-mercapto-6-methylene-7α-methylandrost-4-ene-3,17-dione;
4-mercapto-6-methylene-16α-fluoroandrost-4-ene-3,17-dione;
4-mercapto-6-methylene-16β-fluoroandrost-4-ene-3,17-dione;
4-mercapto-6-methylene-7α-methyl-16α-fluoroandrost-4-ene-3,17-dione;
4-mercapto-6-methylene-7α-methyl-16β-fluoroandrost-4-ene-3,17-dione;
4-mercapto-6-methylenandrosta-1,4-diene-3,17-dione;
4-mercapto-6-methylene-7α-methylandrosta-1,4-diene-3,17-dione;
4-mercapto-6-methylene-16α-fluoroandrosta-1,4-diene-3,17-dione;
4-mercapto-6-methylene-16β-fluoroandrosta-1,4-diene-3,17-dione;
4-mercapto-6-methylene-7α-methyl-16α-fluoroandrosta-1,4-diene-3,17-dione;
4-mercapto-6-methylene-7α-methyl-16β-fluoroandrosta-1,4-diene-3,17-dione;
1-methyl-4-mercapto-6-methylenandrosta-1,4-diene-3,17-dione;
1,7α-dimethyl-4-mercapto-6-methylenandrosta-1,4-diene-3,17-dione;
1-methyl-4-mercapto-6-methylene-16α-fluoroandrosta-1,4-diene-3,17-dione;
1-methyl-4-mercapto-6-methylene-1β-fluoroandrosta-1,4-diene-3,17-dione;
1,7α-dimethyl-4-mercapto-6-methylene-16α-fluoroandrosta-1,4-diene-3,17-dione; and
1,7α-dimethyl-4-mercapto-6-methylene-16β-fluoroandrosta-1,4-diene-3,17-dione.

EXAMPLE VIII 4-ethylthio-6-methylenandrost-4-ene-3,17-dione (I, R=SCH$_2$CH$_3$, R$_1$=R$_2$=R$_3$=R$_4$=H, (x)=single bond)

To a stirred solution of 4,5-epoxy-6-methylenandrostane-3,17-dione (0.78 g, 2.47 mmole) in dioxane (30 ml) is added ethyl thiol (1.5 ml) and polyphosphoric acid (1.5 g) at room temperature under nitrogen. The reaction mixture is stirred for 6 hours and allowed to stand for a further 40 hours, then it is poured into a mixture of water and crushed ice, neutralised with sodium bicarbonate (3 g) and extracted with ethyl acetate. The combined extracts are washed with brine and dried over sodium sulfate. The solution is evaporated in vacuo and the resulting residue is column chromatographed over silica gel. Elution with benzene affords 3,4-bis(ethylthio)-6-methylenandrost-3-ene-17-one (0.410 g). Further elution with benzene: ethyl acetate 90:10 affords the title product. The former product dissolved in chloroform (30 ml) is treated with gaseous HCl during 3 hrs with cooling to give, after evaporation of the solvent, more title product (0.20 g). The two aliquots are combined and crystallised from methanol to yield the title compound (0.350 g, 40% yield), m.p. 140°-5° C., Elemental analysis: Calculated % (found %): C 73.74 (73.61). H 8.37 (8.44). S 8.93 (9.01).

I.R. (KBr, cm$^{-1}$): 1740, 1680, 1555.

In analogous fashion and starting from the appropriate precursors of formula (II) the following compounds can be prepared:

4-ethylthio-6-methylene-7α-methylandrost-4-ene-3,17-dione;
4-ethylthio-6-methylene-16α-fluoroandrost-4-ene-3,17-dione;
4-ethylthio-6-methylene-16β-fluoroandrost-4-ene-3,17-dione;
4-ethylthio-6-methylene-7α-methyl-16α-fluoroandrost-4-ene-3,17-dione;
4-ethylthio-6-methylene-7α-methyl-16β-fluoroandrost-4-ene-3,17-dione;
1-methyl-4-ethylthio-6-methylenandrosta-1,4-diene-3,17-dione;
1,7α-dimethyl-4-ethylthio-6-methylenandrosta-1,4-diene-3,17-dione;
1-methyl-4-ethylthio-6-methylene-16α-fluoroandrosta-1,4-diene-3,17-dione;
1-methyl-4-ethylthio-6-methylene-16β-fluoroandrosta-1,4-diene-3,17-dione;
1,7α-dimethyl-4-ethylthio-6-methylene-16α-fluoroandrosta-1,4-diene-3,17-dione;
1,7α-dimethyl-4-ethylthio-6-methylene-16β-fluoroandrosta-1,4-diene-3,17-dione;
4-ethylthio-6-methylenandrosta-1,4-diene-3,17-dione;
4-ethylthio-6-methylene-7α-methylandrosta-1,4-diene-3,17-dione;
4-ethylthio-6-methylene-16α-fluoroandrosta-1,4-diene-3,17-dione;
4-ethylthio-6-methylene-16β-fluoroandrosta-1,4-diene-3,17-dione;
4-ethylthio-6-methylene-7α-methyl-16α-fluoroandrosta-1,4-diene-3,17-dione; and
4-ethylthio-6-methylene-7α-methyl-16β-fluoroandrosta-1,4-diene-3,17-dione.

EXAMPLE IX 4-acetoxy-6-methylenandrost-4-ene-3,17-dione (I, R=—OCOCH$_3$, R$_1$=R$_2$=R$_3$=R$_4$=H, (x)=single bond)

To a cooled solution of 4-hydroxy-6-methylenandrost-4-ene-3,17-dione (0.40 g, 1.27 mmole) in dry pyridine (3 ml) is added acetic anhydride (1 ml).

The mixture is kept at 0°-5° C. overnight, then it is poured into cold water. The resulting precipitate is filtered off, thoroughly washed with water, dried in vacuo and crystallised from methanol: acetone 50:40.

There are obtained 0.35 g (77% yield) of the title compound, m.p.: 183°-5° C.

In analogous fashion and starting from the appropriate precursors of formula (II) the following compounds can be prepared:

4-acetoxy-6-methylene-7α-methylandrost-4-ene-3,17-dione;
4-acetoxy-6-methylene-16α-fluoroandrost-4-ene-3,17-dione;
4-acetoxy-6-methylene-16β-fluoroandrost-4-ene-3,17-dione;
4-acetoxy-6-methylene-7α-methyl-16α-fluoroandrost-4-ene-3,17-dione;
4-acetoxy-6-methylene-7α-methyl-16β-fluoroandrost-4-ene-3,17-dione;
4-acetoxy-6-methylenandrosta-1,4-diene-3,17-dione;
4-acetoxy-6-methylene-7α-methylandrosta-1,4-diene-3,17-dione;
4-acetoxy-6-methylene-16α-fluoroandrosta-1,4-diene-3,17-dione;
4-acetoxy-6-methylene-16β-fluoroandrosta-1,4-diene-3,17-dione;
4-acetoxy-6-methylene-7α-methyl-16α-fluoroandrosta-1,4-diene-3,17-dione;
4-acetoxy-6-methylene-7α-methyl-16β-fluoroandrosta-1,4-diene-3,17-dione;
1-methyl-4-acetoxy-6-methylenandrosta-1,4-diene-3,17-dione;
1,7α-dimethyl-4-acetoxy-6-methylenadrosta-1,4-diene-3,17-dione;
1-methyl-4-acetoxy-6-methylene-16α-fluoroandrosta-1,4-diene-3,17-dione;
1-methyl-4-acetoxy-6-methylene-16β-fluoroandrosta-1,4-diene-3,17-dione;
1,7α-dimethyl-4-acetoxy-6-methylene-16α-fluoroandrosta-1,4-diene-3,17-dione;
1,7α-dimethyl-4-acetoxy-6-methylene-16β-fluoroandrosta-1,4-diene-3,17-dione;
4-acetylthio-6-methylenandrost-4-ene-3,17-dione;
4-acetylthio-6-methylene-7α-methylandrost-4-ene-3,17-dione;
4-acetylthio-6-methylene-16α-fluoroandrost-4-ene-3,17-dione;
4-acetylthio-6-methylene-16β-fluoroandrost-4-ene-3,17-dione;
4-acetylthio-6-methylene-7α-methyl-16α-fluoroandrost-4-ene-3,17-dione;
4-acetylthio-6-methylene-7α-methyl-16β-fluoroandrost-4-ene-3,17-dione;
4-acetylthio-6-methylenandrosta-1,4-diene-3,17-dione;
4-acetylthio-6-methylene-7α-methylandrosta-1,4-diene-3,17-dione;
4-acetylthio-6-methylene-16α-fluoroandrosta-1,4-diene-3,17-dione;
4-acetylthio-6-methylene-16β-fluoroandrosta-1,4-diene-3,17-dione;
4-acetylthio-6-methylene-7α-methyl-16α-fluoroandrosta-1,4-diene-3,17-dione;
4-acetylthio-6-methylene-7α-methyl-16β-fluoroandrosta-1,4-diene-3,17-dione;
1-methyl-4-acetylthio-6-methylenandrosta-1,4-diene-3,17-dione;
1,7α-dimethyl-4-acetylthio-6-methylenandrosta-1,4-diene-3,17-dione;
1-methyl-4-acetylthio-6-methylene-16α-fluoroandrosta-1,4-diene-3,17-dione;
1-methyl-4-acetylthio-6-methylene-16β-fluoroandrosta-1,4-diene-3,17-dione;

1,7α-dimethyl-4-acetylthio-6-methylene-16α-fluoroandrosta-1,4-diene-3,17-dione; and 1,7α-dimethyl-4-acetylthio-6-methylene-16β-fluoroandrosta-1,4-diene-3,17-dione.

EXAMPLE X 4-methoxy-6-methylenandrost-4-ene-3,17-dione (I, R=OCH$_3$, R$_1$=R$_2$=R$_3$=R$_4$=H, (x)=single bond)

To a solution of 4-hydroxy-6-methylenandrost-4-ene-3,17-dione (0.315 g, 1 mmole) in benzene (10 ml) potassium tert-butoxide (0.224 g, 2 mmole) is added and the mixture heated to reflux for 30 minutes. After cooling, iodomethane (0.710 g, 5 mmole) is added and the mixture boiled for a further 2 hours. Then the organic solution is washed with water, dried and evaporated in vacuum. Flash column chromatography of the residue on silica gel using n-hexane/ethyl acetate 60:40 affords 0.247 g (75% yield) of the title compound, m.p. 196°–198° C.

Elemental analysis:
Calculated % (found %): C 76.83 (76.40). H 8.59 (8.50).

NMR (CDl$_3$,δ): 0.90 (3H, s), 1.14 (3H, s), 3.60 (3H, s), 5.10 (1H, dd), 5.30 (1H, dd).

In analogous fashion and starting from the appropriate 4-hydroxy derivative all the other compounds mentioned in Example V can be prepared.

EXAMPLE XI

Tablets each weighing 0.150 g and containing 25 mg of the active substance, can be manufactured as follows:

| Composition (for 10,000 tablets) | |
| --- | --- |
| 4-methoxy-6-methylenandrost-4-ene-3,17-dione | 250 g |
| Lactose | 800 g |
| Corn starch | 415 g |
| Talc powder | 30 g |
| Magnesium stearate | 5 g |

The 4-methoxy-6-methylenandrost-4-ene-3,17-dione, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate is added, carefully mixed and processed into tablets.

EXAMPLE XII

Capsules, each dosed at 0.200 g and containing 20 mg of the active substance can be prepared with the following composition for 500 capsules:

| 4-hydroxy-6-methylenandrost-4-ene-3,17-dione | 10 g |
| --- | --- |
| Lactose | 80 g |
| Corn starch | 5 g |
| Magnesium stearate | 5 g |

This formulation can be encapsulated in two-piece hard gelatin capsules and dosed at 0.200 g for each capsule.

We claim:

1. A compound of formula (I)

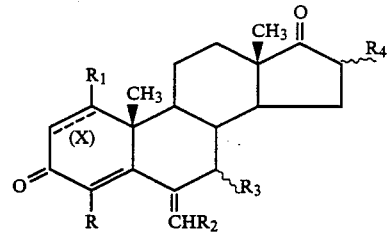

wherein
each of R$_1$, R$_2$ and R$_3$, independently, is hydrogen or C$_1$–C$_6$ alkyl; R$_4$ is hydrogen or fluorine;
the symbol ===== indicates that (x) may be either a single bond or a double bond;
R is
 (1) a group —OR$_5$ wherein R$_5$ is
  (a) hydrogen;
  (b) C$_1$–C$_6$ alkyl;
  (c) a phenyl or benzyl group, each unsubstituted or ring-substituted by one or more substituents chosen from C$_1$–C$_4$ alkyl, halogne, trifluoromethyl, nitro, amino, hydroxy and C$_1$–C$_4$ alkoxy;
  (d) a group —COR$_6$ wherein R$_6$ is
   (i) a C$_1$–C$_{22}$ saturated or C$_2$–C$_{22}$ unsaturated aliphatic hydrocarbon radical;
   (ii) a C$_4$–C$_7$ monocycloalkyl group; or
   (iii) a phenyl or benzyl group, each unsubstituted or ring substituted as reported above; or
  (e) a hydroxy protecting group;
 (2) a group —SR$_7$ wherein R$_7$ either has one of the meanings (a) to (d) indicated above for R$_5$ or is a group —SR$_8$ wherein R$_8$ is
  (iv) C$_1$–C$_6$ alkyl;
  (v) a phenyl or benzyl group, each unsubstituted or ring-substituted as reported above; or
  (vi) a steroidic residue of formula

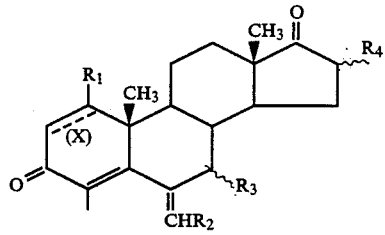

wherein R$_1$, R$_2$, R$_3$, R$_4$ and (x) are as defined above
 (3) the group —N$_3$; or
 (4) a group

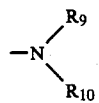

wherein each of R$_9$ and R$_{10}$, independently, is hydrogen or C$_1$–C$_6$ alkyl;
and the pharmaceutically acceptable salts thereof.

2. A compound of formula (I) according to claim 1 wherein each of $R_1$, $R_2$ and $R_3$, independently, is hydrogen or $C_1$–$C_6$ alkyl;

$R_4$ is hydrogen or fluorine;

(x) represents a single bond or a double bond; and R is a group —$OR_5$ or a group —$SR_7$ wherein $R_5$ or, respectively, $R_7$ is hydrogen, $C_1$–$C_6$ alkyl or a group —$COR_6$ wherein $R_6$ is $C_1$–$C_{17}$ alkyl.

3. A compound according to claim 2 selected from the group consisting of:
4-hydroxy-6-methylenandrost-4-ene-3,17-dione;
4-hydroxy-6-methylene-7α-methylandrost-4-ene-3,17-dione;
4-hydroxy-6-methylene-16α-fluoroandrost-4-ene-3,17-dione;
4-hydroxy-6-methylene-16β-fluoroandrost-4-ene-3,17-dione;
4-hydroxy-6-methylene-7α-methyl-16α-fluoroandrost-4-ene-3,17-dione;
4-hydroxy-6-methylene-7α-methyl-16α-fluoroandrost-4-ene-3,17-dione;
4-methoxy-6-methylenandrost-4-ene-3,17-dione;
4-methoxy-6-methylene-7α-methylandrost-4-ene-3,17-dione;
4-methoxy-6-methylene-16α-fluoroandrost-4-ene-3,17-dione;
4-methoxy-6-methylene-16β-fluoroandrost-4-ene-3,17-dione;
4-methoxy-6-methylene-7α-methyl-16α-fluoroandrost-4-ene-3,17-dione;
4-methoxy-6-methylene-7α-methyl-16β-fluoroandrost-4-ene-3,17-dione;
4-acetoxy-6-methylenandrost-4-ene-3,17-dione;
4-acetoxy-6-methylene-7α-methylandrost-4-ene-3,17-dione;
4-acetoxy-6-methylene-16α-fluoroandrost-4-ene-3,17-dione;
4-acetoxy-6-methylene-16β-fluoroandrost-4-ene-3,17-dione;
4-acetoxy-6-methylene-7α-methyl-16α-fluoroandrost-4-ene-3,17-dione;
4-acetoxy-6-methylene-7α-methyl-16β-fluoroandrost-4-ene-3,17-dione;
4-hydroxy-6-methylenandrosta-1,4-diene-3,17-dione;
4-hydroxy-6-methylene-7α-methylandrosta-1,4-diene-3,17-dione;
4-hydroxy-6-methylene-16α-fluoroandrosta-1,4-diene-3,17-dione;
4-hydroxy-6-methylene-16β-fluoroandrosta-1,4-diene-3,17-dione;
4-hydroxy-6-methylene-7α-methyl-16α-fluoroandrosta-1,4-diene-3,17-dione;
4-hydroxy-6-methylene-7α-methyl-16β-fluoroandrosta-1,4-diene-3,17-dione;
4-hydroxy-6-methylenandrosta-1,4-diene-3,17-dione;
4-methoxy-6-methylene-7α-methylandrosta-1,4-diene-3,17-dione;
4-methoxy-6-methylene-16α-fluoroandrosta-1,4-diene-3,17-dione;
4-methoxy-6-methylene-16β-fluoroandrosta-1,4-diene-3,17-dione;
4-methoxy-6-methylene-7α-methyl-16α-fluoroandrosta-1,4-diene-3,17-dione;
4-methoxy-6-methylene-7α-methyl-16β-fluoroandrosta-1,4-diene-3,17-dione;
4-acetoxy-6-methylenandrosta-1,4-diene-3,17-dione;
4-acetoxy-6-methylene-7α-methylandrosta-1,4-diene-3,17-dione;
4-acetoxy-6-methylene-16α-fluoroandrosta-1,4-diene-3,17-dione;
4-acetoxy-6-methylene-16β-fluoroandrosta-1,4-diene-3,17-dione;
4-acetoxy-6-methylene-7α-methyl-16α-fluoroandrosta-1,4-diene-3,17-dione;
4-acetoxy-6-methylene-7α-methyl-16β-fluoroandrosta-1,4-diene-3,17-dione;
1-methyl-4-hydroxy-6-methylenandrosta-1,4-diene-3,17-dione;
1,7α-dimethyl-4-hydroxy-6-methylenandrosta:1,4-diene-3,17-dione;
1-methyl-4-hydroxy-6-methylene-16α-fluoroandrosta-1,4-diene-3,17-dione;
1-methyl-4-hydroxy-6-methylene-16β-fluoroandrosta-1,4-diene-3,17-dione;
1,7α-dimethyl-4-hydroxy-6-methylene-16α-fluoroandrosta-1,4-diene-3,17-dione;
1,7α-dimethyl-4-hydroxy-6-methylene-16β-fluoroandrosta-1,4-diene-3,17-dione;
1-methyl-4-methoxy-6-metylenandrosta-1,4-diene-3,17-dione;
1,7α-dimethyl-4-methoxy-6-methylenandrosta-1,4-diene-3,17-dione;
1-methyl-4-methoxy-6-methylene-16α-fluoroandrosta-1,4-diene-3,17-dione;
1-methyl-4-methoxy-6-methylene-16β-fluoroandrosta-1,4-diene-3,17-dione;
1,7α-dimethyl-4-methoxy-6-methylene-16α-fluoroandrosta-1,4-diene-3,17-dione;
1,7α-dimethyl-4-methoxy-6-methylene-16β-fluoroandrosta-1,4-diene-3,17-dione;
1-methyl-4-acetoxy-6-methylenandrosta-1,4-diene-3,17-dione;
1,7α-dimethyl-4-acetoxy-6-methylenandrosta-1,4-diene-3,17-dione;
1-methyl-4-acetoxy-6-methylene-16α-fluoroandrosta-1,4-diene-3,17-dione;
1-methyl-4-acetoxy-6-methylene-16β-fluoroandrosta-1,4-diene-3,17-dione;
1,7α-dimethyl-4-acetoxy-6-methylene-16α-fluoroandrosta-1,4-diene-3,17-dione;
1,7α-dimethyl-4-acetoxy-6-methylene-16β-fluoroandrosta-1,4-diene-3,17-dione;
4-mercapto-6-methylenandrost-4-ene-3,17-dione;
4-mercapto-6-methylene-7α-methylandrost-4-ene-3,17-dione;
4-mercapto-6-methylene-16α-fluoroandrost-4-ene-3,17-dione;
4-mercapto-6-methylene-16β-fluoroandrost-4-ene-3,17-dione;
4-mercapto-6-methylene-7α-methyl-16α-fluoroandrost-4-ene-3,17-dione;
4-mercapto-6-methylene-7α-methyl-16β-fluoroandrost-4-ene-3,17-dione;
4-acetylthio-6-methylenandrost-4-ene-3,17-dione;
4-acetylthio-6-methylene-7α-methylandrost-4-ene-3,17-dione;
4-acetylthio-6-methylene-16α-fluoroandrost-4-ene-3,17-dione;
4-acetylthio-6-methylene-16β-fluoroandrost-4-ene-3,17-dione;
4-acetylthio-6-methylene-7α-methyl-16α-fluoroandrost-4-ene-3,17-dione;
4-acetylthio-6-methylene-7α-methyl-16β-fluoroandrost-4-ene-3,17-dione;
4-ethylthio-6-methylenandrost-4-ene-3,17-dione;

4-ethylthio-6-methylene-7α-methylandrost-4-ene-3,17-dione;
4-ethylthio-6-methylene-16α-fluoroandrost-4-ene-3,17-dione;
4-ethylthio-6-methylene-16β-fluoroandrost-4-ene-3,17-dione;
4-ethylthio-6-methylene-7α-methyl-16α-fluoroandrost-4-ene-3,17-dione;
4-ethylthio-6-methylene-7α-methyl-16β-fluoroandrost-4-ene-3,17-dione;
4-mercapto-6-methylenandrosta-1,4-diene-3,17-dione;
4-mercapto-6-methylene-7α-methylenandrosta-1,4-diene-3,17-dione;
4-mercapto-6-methylene-16α-fluoroandrosta-1,4-diene-3,17-dione;
4-mercapto-6-methylene-16β-fluoroandrosta-1,4-diene-3,17-dione;
4-mercapto-6-methylene-7α-methyl-16α-fluoroandrosta-1,4-diene-3,17-dione;
4-mercapto-6-methylene-7α-methyl-16β-fluoroandrosta-1,4-diene-3,17-dione;
4-acetylthio-6-methylenandrosta-1,4-diene-3,17-dione;
4-acetylthio-6-methylene-7α-methylandrosta-1,4-diene-3,17-dione;
4-acetylthio-6-methylene-16α-fluoroandrosta-1,4-diene-3,17-dione;
4-acetylthio-6-methylene-16β-fluoroandrosta-1,4-diene-3,17-dione;
4-acetylthio-6-methylene-7α-methyl-16α-fluoroandrosta-1,4-diene-3,17-dione;
4-acetylthio-6-methylene-7α-methyl-16β-fluoroandrosta-1,4-diene-3,17-dione;
4-ethylthio-6-methylenandrosta-1,4-diene-3,17-dione;
4-ethylthio-6-methylene-7α-methylandrosta-1,4-diene-3,17-dione;
4-ethylthio-6-methylene-16α-fluoroandrosta-1,4-diene-3,17-dione;
4-ethylthio-6-methylene-16β-fluoroandrosta-1,4-diene-3,17-dione;
4-ethylthio-6-methylene-7α-methyl-16α-fluoroandrosta-1,4-diene-3,17-dione;
4-ethylthio-6-methylene-7α-methyl-16β-fluoroandrosta-1,4-diene-3,17-dione;
1-methyl-4-mercapto-6-methylenandrosta-1,4-diene-3,17-dione;
1,7α-dimethyl-4-mercapto-6-methylenandrosta-1,4-diene-3,17-dione;
1-methyl-4-mercapto-6-methylene-16β-fluoroandrosta-1,4-diene-3,17-dione;
1-methyl-4-mercapto-6-methylene-16-β-fluoroandrosta-1,4-diene-3,17-dione;
1,7α-dimethyl-4-mercapto-6-methylene-16α-fluoroandrosta-1,4-diene-3,17-dione;
1,7α-dimethyl-4-mercapto-6-methylene-16β-fluoroandrosta-1,4-diene-3,17-dione;
1-methyl-4-acetylthio-6-methylenandrosta-1,4-diene-3,17-dione;
1,7α-dimethyl-4-acetylthio-6-methylenandrosta-1,4-diene-3,17-dione;
1-methyl-4-acetylthio-6-methylene-16α-fluoroandrosta-1,4-diene-3,17-dione;
1-methyl-4-acetylthio-6-methylene-16β-fluoroandrosta-1,4-diene-3,17-dione;
1,7α-dimethyl-4-acetylthio-6-methylene-16α-fluoroandrosta-1,4-diene-3,17-dione;
1,7α-dimethyl-4-acetylthio-6-methylene-16β-fluoroandrosta-1,4-diene-3,17-dione;
1-methyl-4-ethylthio-6-methylenandrosta-1,4-diene-3,17-dione;
1,7α-dimethyl-4-ethylthio-6-methylenandrosta-1,4-diene-3,17-dione;
1-methyl-4-ethylthio-6-methylene-16β-fluoroandrosta-1,4-diene-3,17-dione;
1-methyl-4-ethylthio-6-methylene-16β-fluoroandrosta-1,4-diene-3,17-dione;
1,7α-dimethyl-4-ethylthio-6-methylene-16α-fluoroandrosta-1,4-diene-3,17-dione; and
1,7α-dimethyl-4-ethylthio-6-methylene-16β-fluoroandrosta-1,4-diene-3,17-dione.

4. A compound of formula (I) according to claim 1 wherein
each of $R_1$, $R_2$ and $R_3$, independently, is hydrogen or $C_1$-$C_6$ alkyl;
$R_4$ is hydrogen or fluorine;
(x) represents a single bond or a double bond; and
R is a group $$-N\begin{matrix}R_9\\R_{10}\end{matrix}$$

wherein one of $R_9$ and $R_{10}$ is hydrogen and the other is hydrogen or $C_1$-$C_6$ alkyl;
and the pharmaceutically acceptable salts thereof.

5. A compound according to claim 4 selected from the group consisting of:
4-amino-6-methylenandrost-4-ene-3,17-dione;
4-amino-6-methylene-7α-methylandrost-4-ene-3,17-dione;
4-amino-6-methylene-16α-fluoroandrost-4-ene-3,17-dione;
4-amino-6-methylene-16β-fluoroandrost-4-ene-3,17-dione;
4-amino-6-methylene-7α-methyl-16α-fluoroandrost-4-ene-3,17-dione;
4-amino-6-methylene-7α-methyl-16β-fluoroandrost-4-ene-3,17-dione;
4-amino-6-methylenandrosta-1,4-diene-3,17-dione;
4-amino-6-methylene-7α-methylandrosta-1,4-diene-3,17-dione;
4-amino-6-methylene-16α-fluoroandrosta-1,4-diene-3,17-dione;
4-amino-6-methylene-16β-fluoroandrosta-1,4-diene-3,17-dione;
4-amino-6-methylene-7α-methyl-16α-fluoroandrosta-1,4-diene-3,17-dione;
4-amino-6-methylene-7α-methyl-16β-fluoroandrosta-1,4-diene-3,17-dione;
1-methyl-4-amino-6-methylenandrosta-1,4-diene-3,17-dione;
1,7α-dimethyl-4-amino-6-methylenandrosta-1,4-diene-3,17-dione;
1-methyl-4-amino-6-methylene-16α-fluoroandrosta-1,4-diene-3,17-dione;
1-methyl-4-amino-6-methylene-16β-fluoroandrosta-1,4-diene-3,17-dione;
1,7α-dimethyl-4-amino-6-methylene-16α-fluoroandrosta-1,4-diene-3,17-dione;
1,7α-dimethyl-4-amino-6-methylene-16β-fluoroandrosta-1,4-diene-3,17-dione,
and the pharmaceutically acceptable salts thereof.

* * * * *

UNITED STATES PATENT AND TRADEMARK OFFICE
CERTIFICATE OF CORRECTION

PATENT NO. : 4,822,528
DATED : April 18, 1989
INVENTOR(S) : COLOMBO et al

Page 1 of 2

It is certified that error appears in the above-identified patent and that said Letters Patent is hereby corrected as shown below:

On the cover page, Item [54], "ALKYLIDENANDROSTEINE" should read --ALKYLIDENANDROSTENE--;

Item [57], line 2 after the chemical formula, "hydrogen of fluorine" should read --hydrogen or fluorine--.

Column 1, line 2, "ALKYLIDENANDROSTEINE" should read --ALKYLIDENANDROSTENE--.

Column 3, line 5, "grou" should read --group--;

line 39, "trimethylsylyl" should read --trimethylsilyl--.

Column 8, lines 51 to 61, the chemical formula should appear as follows:

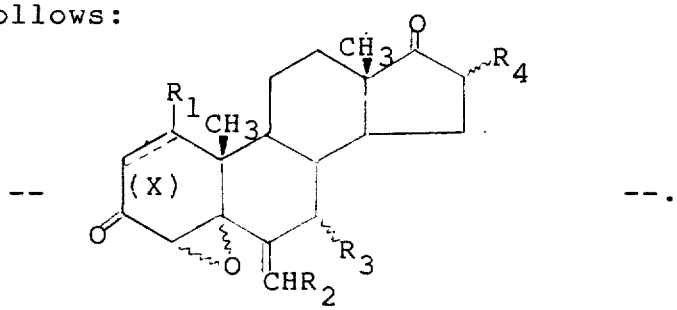

Column 12, line 20, "iodite" should read --iodine--.

Column 13, line 23, "comppounds" should read --compounds--;

line 38, "R and $R_4$" should read --$R_1$ and $R_4$--;

line 65, "Boil." should read --Biol.--.

Column 14, line 55, "di-saggregating" should read --disaggregating--.

Column 15, line 11, "infusione" should read --infusions--.

UNITED STATES PATENT AND TRADEMARK OFFICE
CERTIFICATE OF CORRECTION

PATENT NO. : 4,822,528
DATED : Apirl 18, 1989
INVENTOR(S) : COLOMBO et al

It is certified that error appears in the above-identified patent and that said Letters Patent is hereby corrected as shown below:

Column 16, line 22, "1,17" should read --3,17--;
       line 43, "methyleandrost" should read --methylenandrost--.

Column 24, line 24, "halogne" should read --halogen--.

Column 25, line 20, "16α" should read --16β--.

Column 27, line 50, "16β" should read --16α--.

Column 28, line 7, "16β" should read --16α--.

Signed and Sealed this

Sixteenth Day of January, 1990

*Attest:*

JEFFREY M. SAMUELS

*Attesting Officer*     *Acting Commissioner of Patents and Trademarks*